(12) United States Patent
Desos et al.

(10) Patent No.: US 7,253,163 B2
(45) Date of Patent: Aug. 7, 2007

(54) BENZOTHIAZINE AND BENZOTHIADIAZINE COMPOUNDS

(75) Inventors: Patrice Desos, Bois-Colombes (FR); Alex Cordi, Suresnes (FR); Pierre Lestagé, La Celle Saint Cloud (FR)

(73) Assignee: Les Laboratoires Servier, Courbevoie (FR)

( * ) Notice: Subject to any disclaimer, the term of this patent is extended or adjusted under 35 U.S.C. 154(b) by 23 days.

(21) Appl. No.: 10/865,185

(22) Filed: Jun. 10, 2004

(65) Prior Publication Data

US 2004/0254371 A1 Dec. 16, 2004

(30) Foreign Application Priority Data

Jun. 13, 2003 (FR) .................................. 03 07117

(51) Int. Cl.
*C07D 513/04* (2006.01)
*A61K 31/542* (2006.01)
*A61P 25/24* (2006.01)

(52) U.S. Cl. ....................... 514/222.8; 544/9; 514/215; 540/578

(58) Field of Classification Search .................... 544/9; 514/222.8, 215; 540/578
See application file for complete search history.

(56) References Cited

OTHER PUBLICATIONS

Alt et al. Current Pharmaceutical Design, 2005, 11, 1511-1527.*
Black et al Psychopharmacology (2005) 179: 154-163.*
Daniel DeNoon, Schizophrenia Drug Face-Off: No Clear Winner, from the website http://www.webmd.com/content/Article/112/110297.htm?printing=true, downloaded on May 22, 2006.*
Maskell, et al., *Br. J. Pharmacol*, 2003, 140, 1313-1319.
Aracava, et al., *JPET*, 2005, 312, 1195-1250.
Advokat, et al., *Neurosci. Biobehav. Rev.*, 1992, 16, 13-24.
Danysz, et al., *Behav. Pharmacol.*, 1995, 6, 455-474.
Lynch, *Neurobiology of Learning and Memory*, 1998, 70, 82-100.
Robbins, et al., *TRENDS in Pharmacological Sciences*, 2006, 27 (3), 141-148.
Bliss, et al., *Nature*, 1993, 361, 31-39.
Ito, et al., *Journal of Physiology*, 1990, 424, 533-543.
Cumin, et al., *Psychopharmacology*, 1982, 78, 104-111.
Araj, et al., *Brian Res.*, 1994, 638, 343-346.
Miu, et al., *Neuropharmacol.*, 2001, 40, 976-983.
Staubli, et al., *Proc. Natl. Acad. Sci.*, 1994, 91, 777-781.
Lebrun, et al., *European Journal of Pharmacology*, 2000, 401, 205-212.
Rao, et al., *Neuroscience Letters*, 2001, 298, 183-186.
Thompson, et al., *Proc. Natl. Acad. Sci.*, 1995, 92, 7667-7671.
Buccafusco, et al., *Neuropharmacol.*, 2004, 46, 10-22.
Porrino, et al., *PLOS Biology*, 2005, 3 (9), 1639-1652.
Ingvar, et al., *Exp. Neurol.*, 1997, 146, 553-559.
Lynch, et al., *Exp. Neurol.*, 1997, 145, 89-92.
Baudry, *Neurobiology of Learning and Memory*, 2001, 76, 284-297.
Day, et al., *Nature*, 2003, 424, 205-209.
Lynch, *Current Opinion in Pharmacology*, 2006, 6, 82-88.
Lin, et al., *Brain Research*, 2002, 955, 164-173.
Desai, et al., *Neuropharmacology*, 1995, 34 (2), 141-147.
Lockhart, et al., *European Journal of Pharmacology*, 2000, 401, 145-153.
Jhee, et al., *J. Clin. Pharmacol.*, 2006, 46, 424-432.
Roger, et al., *Soc. Neurosci. Abstr.*, 2004, Abstract No. 219.11.
Dicou, et al., *Brain Research*, 2003, 970, 221-225.
Bahr, et al., *Exp. Neurol.*, 2002, 174, 37-47.
Murray, et al., *JPET*, 2003, 306, 752-762.
O'Neill, et al., *European Journal of Pharmacology*, 2004, 486, 163-174.
O'Neill, et al., *CNS Drug Rev.*, 2005, 11 (1), 77-98.
Bai, et al., *Neuropharmacology*, 2003, 44, 1013-1021.
Lauterborn, et al., *J. of Neuroscience*, 2000, 20 (1), 8-21.
Carrié, et al., *Soc. Neurosci. Abstr.*, 2005, Abstract No. 1018.4.
Lockhart, et al., *Soc. Neurosci. Abstr.*, 2004, Abstract No. 92.12.
Munoz, et al., *Soc. Neurosci. Abstr.*, 2004, Abstract No. 85.13.
Nibuya, et al., *J. of Neuroscience*, 1995, 15 (11), 7539-7547.
Dias, et al., *Neuropharmacology*, 2003, 45, 553-563.
Alt, et al., *Curr. Pharm. Des.*, 2005, 11 (12), 1511-1527.
Alt, et al., *Biochemical Pharmacology*, 2006, 71, 1273-1288.
Nakamura, et al., *Psychopharmacology*, 2001, 158, 205-212.
Li, et al., *Neuropharmacology*, 2001, 40, 1028-1033.
Knapp, et al., *European Journal of Pharmacology*, 2002, 440, 27-35.

* cited by examiner

Primary Examiner—Kahsay Habte
(74) Attorney, Agent, or Firm—Hueschen and Sage

(57) ABSTRACT

Compounds of formula (I):

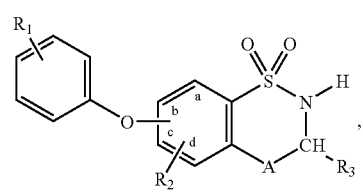

(I)

wherein:
$R_1$ represents a heterocycle,
$R_2$ represents hydrogen, a halogen or hydroxy,
A represents $CR_4R_5$ or $NR_4$,
$R_3$ represents hydrogen, alkyl or cycloalkyl,
$R_4$ represents hydrogen or alkyl,
or
A represents nitrogen and, together with the adjacent —$CHR_3$—, forms the ring

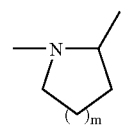

wherein m represents 1, 2 or 3,
$R_5$ represents hydrogen or a halogen,
their isomers, and also addition salts thereof.

14 Claims, No Drawings

BENZOTHIAZINE AND BENZOTHIADIAZINE COMPOUNDS

FIELD OF THE INVENTION

The present invention relates to new benzothiazine and benzothiadiazine compounds, to a process for their preparation and to pharmaceutical compositions containing them. The compounds of the present invention are new and have very valuable pharmacological properties in respect of AMPA receptors.

BACKGROUND OF THE INVENTION

It has now been recognised that the excitatory amino acids, especially glutamate, play a crucial role in the physiological processes of neuronal plasticity and in the mechanisms underlying learning and memory. Pathophysiological studies have clearly shown that a deficit in glutamatergic neurotransmission is closely linked to the development of Alzheimer's disease (Neuroscience and Biobehavioral reviews, 1992, 16, 13-24; Progress in Neurobiology, 1992, 39, 517-545).

In addition, innumerable works have in recent years demonstrated the existence of sub-types of excitatory amino acid receptors and their functional interactions (Molecular Neuropharmacology, 1992, 2, 15-31).

Among those receptors, the AMPA (α-amino-3-hydroxy-5-methyl-4-isoxazole-propionic acid) receptor appears to be involved to the greatest extent in the phenomena of physiological neuronal excitability and, especially, in those phenomena involved in memorisation processes. For example, it has been shown that learning is associated with an increase in the binding of AMPA to its receptor in the hippocampus, one of the areas of the brain essential to processes of memory and cognition. Likewise, nootropic agents such as aniracetam have very recently been described as modulating the AMPA receptors of neuronal cells in a positive manner (Journal of Neurochemistry, 1992, 58, 1199-1204).

DESCRIPTION OF THE PRIOR ART

In the literature, compounds having a benzamide structure have been described as possessing this same mechanism of action and improving memory performance (Synapse, 1993, 15, 326-329). Compound BA 74, in particular, is the most active of those new pharmacological agents.

Finally, patent specification EP 692 484 describes a benzothiadiazine compound having a facilitating action on the AMPA current, and patent application WO 99/42456 describes inter alia particular benzothiadiazine compounds as modulators of AMPA receptors.

The benzothiazine and benzothiadiazine compounds to which the present invention relates, besides being new, surprisingly exhibit pharmacological activity on the AMPA current that is markedly superior to the activity of the compounds having similar structures described in the prior art. They are useful as AMPA modulators for the treatment or prevention of disorders of memory and cognition that are associated with age, with syndromes of anxiety or depression, with progressive neurodegenerative diseases, with Alzheimer's disease, with Pick's disease, with Huntington's chorea, with schizophrenia, with the sequelae of acute neurodegenerative diseases, with the sequelae of ischaemia and with the sequelae of epilepsy.

DETAILED DESCRIPTION OF THE INVENTION

More specifically, the present invention relates to compounds of formula (I):

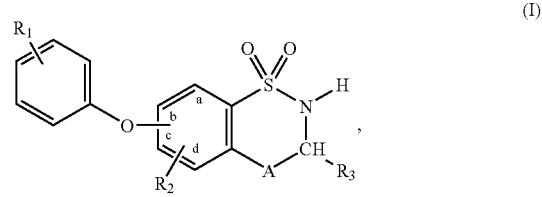

wherein:

$R_1$ represents a heterocyclic group, $R_2$ represents a hydrogen atom, a halogen atom or a hydroxy group, A represents a $CR_4R_5$ group or an $NR_4$ group, $R_3$ represents a hydrogen atom, a linear or branched ($C_1$-$C_6$)alkyl group or a ($C_3$-$C_7$)cycloalkyl group, $R_4$ represents a hydrogen atom or a linear or branched ($C_1$-$C_6$)alkyl group, or A represents a nitrogen atom and, together with the adjacent —$CHR_3$— group, forms the ring

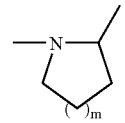

wherein m represents 1, 2 or 3, $R_5$ represents a hydrogen or halogen atom, to their enantiomers and diastereoisomers, and also to addition salts thereof with a pharmaceutically acceptable acid or base, a heterocyclic group being understood to mean a monocyclic or bicyclic, aromatic or non-aromatic group containing from one to four identical or different hetero atoms selected from nitrogen, oxygen and sulphur, optionally substituted by one or more identical or different groups selected from halogen, linear or branched ($C_1$-$C_6$)alkyl, linear or branched ($C_1$-$C_6$)alkoxy, linear or branched ($C_1$-$C_6$)polyhaloalkyl, linear or branched ($C_1$-$C_6$)alkoxycarbonyl, oxo, thioxo, carboxy, linear or branched ($C_1$-$C_6$)acyl, linear or branched ($C_1$-$C_6$)polyhaloalkoxy, hydroxy, cyano, nitro, amino (optionally substituted by one or more linear or branched ($C_1$-$C_6$)alkyl groups), aminosulphonyl (optionally substituted by one or more linear or branched ($C_1$-$C_6$)alkyl groups) and ($C_1$-$C_6$) alkylsulphonylamino.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

The grouping

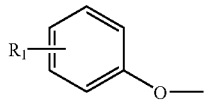

is preferably in position b of the phenyl carrying it.

$R_1$ preferably represents a monocyclic heterocyclic group.

Greater preference is given to $R_1$ representing an aromatic monocyclic heterocyclic group containing from 1 to 4 hetero atoms selected from nitrogen, sulphur and oxygen, more especially nitrogen and oxygen, such as, for example, the tetrazolyl, triazolyl, imidazolyl, pyrazolyl, pyrrolyl, pyridyl, furyl, oxazolyl and oxadiazolyl groups.

In likewise advantageous manner, $R_1$ represents a monocyclic heterocyclic group containing from 1 to 4 hetero atoms selected from oxygen, sulphur and nitrogen, more especially the oxathiadiazolyl, dihydrooxadiazolyl and morpholinyl groups.

Advantageously, the group $R_1$ is unsubstituted or substituted by a linear or branched $(C_1-C_6)$alkyl group such as, for example, the methyl group, or by an oxo or thioxo group.

The $R_1$ group is preferably in the meta- or para-position of the phenoxy ring structure carrying it.

Preference is given to the $R_2$ group being a hydrogen atom.

Preferred compounds of the invention are compounds wherein A represents a nitrogen atom and, together with the adjacent —$CHR_3$— group, forms the ring

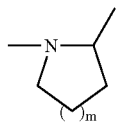

wherein m represents 1, 2 or 3, preferably 1.

Preferred compounds of the invention are 7-[3-(1H-tetrazol-5-yl)phenoxy]-2,3,3a,4-tetrahydro-1H-pyrrolo[2,1-c][1,2,4]benzothiadiazine 5,5-dioxide, 7-[3-(3-furyl)phenoxy]-2,3,3a,4-tetrahydro-1H-pyrrolo[2,1-c][1,2,4]benzothiadiazine 5,5-dioxide and 7-[3-(1,3-oxazol-5-yl)phenoxy]-2,3,3a,4-tetrahydro-1H-pyrrolo[2,1-c][1,2,4]benzothiadiazine.

The enantiomers, diastereoisomers and addition salts with a pharmaceutically acceptable acid or base of the preferred compounds of the invention form an integral part of the invention.

The invention relates also to the processes for the preparation of compounds of formula (I).

The process for the preparation of compounds of formula (I) wherein A represents an $NR_4$ group or A represents a nitrogen atom and, together with the adjacent $CHR_3$ group, forms the ring

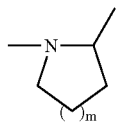

wherein m represents 1, 2 or 3, is characterised in that there is used as starting material a compound of formula (II):

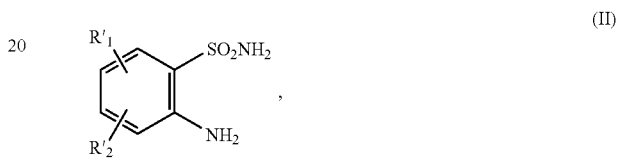

wherein:

$R'_1$ represents a linear or branched $(C_1-C_6)$alkoxy group, $R'_2$ represents a hydrogen atom, a halogen atom or a linear or branched $(C_1-C_6)$alkoxy group, which is:

(a) either reacted with the acid chloride of formula (III) in the presence of a base, in a tetrahydrofuran or acetonitrile medium:

wherein m is as defined for formula (I), to yield the compound of formula (IV):

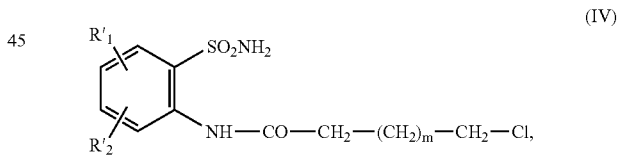

wherein $R'_1$ and $R'_2$ are as defined hereinbefore, which is then cyclised in a basic medium to yield the compound of formula (V):

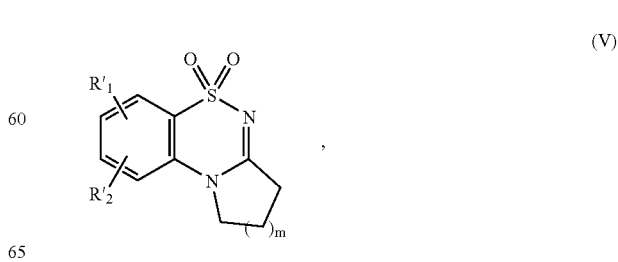

wherein $R'_1$, $R'_2$ and m are as defined hereinbefore, which is optionally subjected to reduction, in an alcoholic or
dimethylformamide medium, in the presence of sodium
borohydride, to yield the compound of formula (VI):

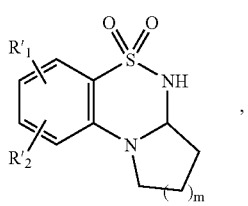
(VI)

wherein R'$_1$, R'$_2$ and m are as defined hereinbefore,
which compound of formula (V) or (VI) is subjected to the action of boron tribromide
to yield the compound of formula (VII):

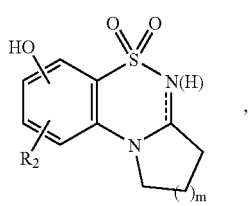
(VII)

wherein R$_2$ is as defined for formula (I) and m is as defined hereinbefore,
(b) or cyclised:
in the presence of an amidine of formula (VIII):

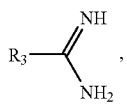
(VIII)

wherein:
R$_3$ is as defined for formula (I),
to yield the compound of formula (IX):

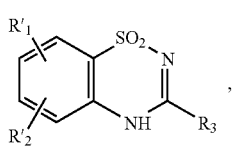
(IX)

wherein R'$_1$, R'$_2$ and R$_3$ are as defined hereinbefore,
which is:
either reduced, using a metallic hydride,
to yield the compound of formula (X):

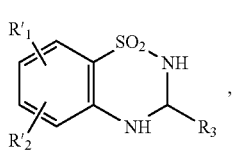
(X)

wherein R'$_1$, R'$_2$ and R$_3$ are as defined hereinbefore,
or alkylated by the action of a strong base in the presence of an alkylating agent R'$_4$X,
wherein R'$_4$ represents a linear or branched (C$_1$-C$_6$)alkyl group and X represents a halogen atom, and then reduced
to yield the compound of formula (XI):

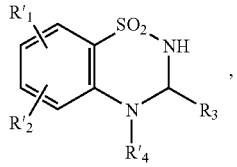
(XI)

wherein R'$_1$, R'$_2$, R$_3$ and R'$_4$ are as defined hereinbefore,
in the presence of an aldehyde of formula (XII):

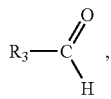
(XII)

wherein R$_3$ is as defined for formula (I),
to yield the compound of formula (X) described hereinbefore,
in which compound of formula (X) or (XI)
the group R'$_1$ and, when the group R'$_2$ represents a linear or branched (C$_1$-C$_6$)alkoxy group,
the group R'$_2$ are converted into hydroxy groups
to yield the compound of formula (XIII):

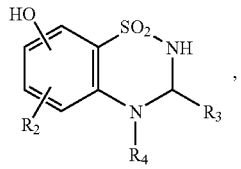
(XIII)

wherein R$_2$, R$_3$ and R$_4$ are as defined for formula (I),
which compound of formula (VII) or (XIII) is reacted with a boronic acid compound of formula (XIV):

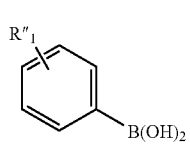
(XIV)

wherein R''$_1$ represents a cyano group or a heterocycle,
to yield (after optional conversion of the group R''$_1$, when the latter represents a cyano group, into the corresponding tetrazolyl group) the compound of formula (I/a$_1$) or (I/a$_2$),
particular cases of the compounds of formula (I):

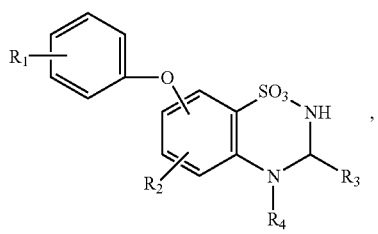
(I/a$_1$)

wherein $R_1$, $R_2$, $R_3$ and $R_4$ are as defined for formula (I), (I/a₂)

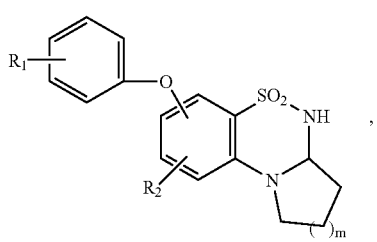

wherein $R_1$, $R_2$ and m are as defined for formula (I),
which compounds of formulae (I/a₁) and (I/a₂):
are purified, if necessary, according to a conventional purification technique, are separated, if desired, into their isomers according to a conventional separation technique and are converted, if desired, into their addition salts with a pharmaceutically acceptable acid or base.

The process for the preparation of compounds of formula (I) wherein A represents a $CR_4R_5$ group is characterised in that there is used as starting material a compound of formula (XV):

(XV)

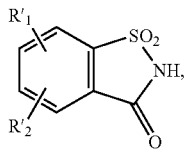

wherein:
$R'_1$ represents a linear or branched ($C_1$-$C_6$)alkoxy group,
$R'_2$ represents a hydrogen atom, a halogen atom or a linear or branched ($C_1$-$C_6$)alkoxy group,
which is subjected to the action of chloroacetone in the presence of dimethylformamide to yield the compound of formula (XVI):

(XVI)

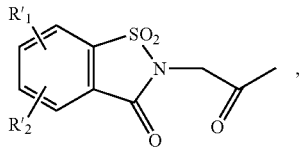

wherein $R'_1$ and $R'_2$ are as defined hereinbefore,
which is subjected to a rearrangement in a basic medium to yield the compound of formula (XVII):

(XVII)

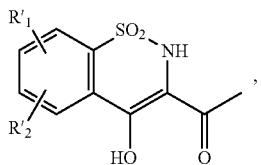

wherein $R'_1$, and $R'_2$ are as defined hereinbefore,
which is deacetylated by heating at reflux in a benzene medium in the presence of an excess of ethylene glycol and a catalytic amount of p-toluenesulphonic acid to yield the compound of formula (XVIII):

(XVIII)

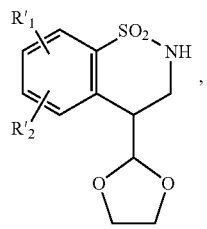

wherein $R'_1$, and $R'_2$ are as defined hereinbefore,
which is subjected to hydrolysis in an acid medium to yield the compound of formula (XIXa):

(XIXa)

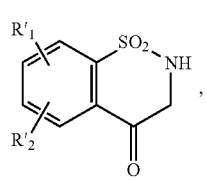

wherein $R'_1$, and $R'_2$ are as defined hereinbefore,
the nitrogen atom of which is optionally, depending on the nature of the group $R_3$ that is desired, protected by a protecting group and which is then, after treatment with a strong base, treated with a compound of formula $R'_3$-P,
wherein $R'_3$ represents a linear or branched ($C_1$-$C_6$)alkyl group or a ($C_3$-$C_7$)cycloalkyl group and P represents a leaving group,
to yield, after deprotection of the nitrogen atom, the compound of formula (XIX'a):

(XIX'a)

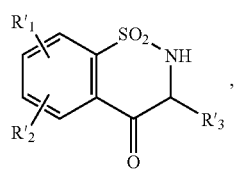

wherein $R'_1$, $R'_2$ and $R'_3$ are as defined hereinbefore,
which compound of formula (XIXa) or (XIX'a), represented by formula (XIX):

(XIX)

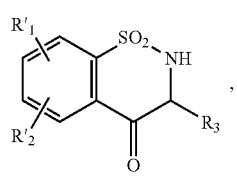

wherein R'$_1$, and R'$_2$ are as defined hereinbefore and R$_3$ is as defined for formula (I), is:

either subjected to catalytic reduction to yield the compound of formula (XX):

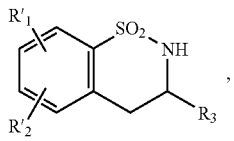

(XX)

wherein R'$_1$, and R'$_2$ are as defined hereinbefore, or converted by the action of a hydride into an alcohol, the hydroxy group of which is converted into a halogen atom by the action of an appropriate reagent to yield the compound of formula (XXI):

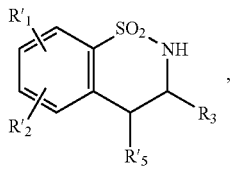

(XXI)

wherein R'$_1$, R'$_2$ and R$_3$ are as defined hereinbefore and R'$_5$ represents a halogen atom, or subjected to the action of an organomagnesium compound R'$_4$MgBr, wherein R'$_4$ represents a linear or branched (C$_1$-C$_6$)alkyl group, to yield the compound of formula (XIXb):

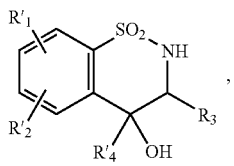

(XIXb)

wherein R'$_1$, R'$_2$, R$_3$ and R'$_4$ are as defined hereinbefore, which compound of formula (XIXb)

either is subjected to catalytic reduction to yield the compound of formula (XXII):

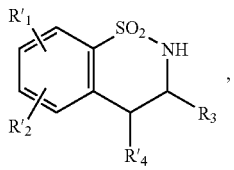

(XXII)

wherein R'$_1$, R'$_2$, R$_3$ and R'$_4$ are as defined hereinbefore, or the hydroxy group thereof is converted into a halogen atom by the action of an appropriate reagent to yield the compound of formula (XXIII):

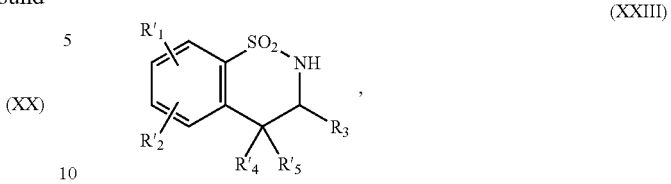

(XXIII)

wherein R'$_1$, R'$_2$, R$_3$ and R'$_4$ are as defined hereinbefore and R'$_5$ represents a halogen atom, in which compounds of formulae (XX) to (XXIII) the group R'$_1$ and, when the group R'2 represents a linear or branched (C$_1$-C$_6$)alkoxy group, the group R'$_2$ are converted into hydroxy groups to yield the compound of formula (XXIV):

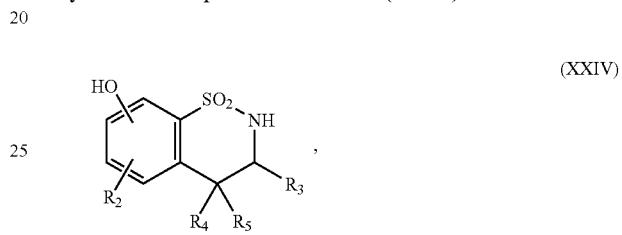

(XXIV)

wherein R$_2$, R$_3$, R$_4$ and R$_5$ are as defined for formula (I), which compound of formula (XXIV)

is reacted with a boronic acid compound of formula (XIV):

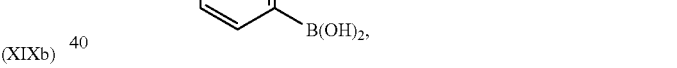

(XIV)

wherein R''$_1$ represents a cyano group or a heterocycle, to yield (after optional conversion of the group R''$_1$, when the latter represents a cyano group, into the corresponding tetrazolyl group) the compound of formula (I/b), a particular case of the compounds of formula (I):

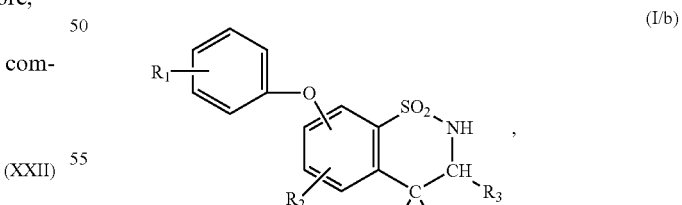

(I/b)

wherein R$_1$, R$_2$, R$_3$, R$_4$ and R$_5$ are as defined for formula (I), which compound of formula (I/b) is purified, if necessary, according to a conventional purification technique, is separated, if desired, into its isomers according to a conventional separation technique and is converted, if desired, into its addition salts with a pharmaceutically acceptable acid or base.

The invention relates also to pharmaceutical compositions comprising, as active ingredient, a compound of formula (I) with one or more appropriate, inert, non-toxic excipients. Among the pharmaceutical compositions according to the invention there may be mentioned more especially those that are suitable for oral, parenteral (intravenous or subcutaneous) or nasal administration, tablets or dragées, sublingual tablets, gelatin capsules, lozenges, suppositories, creams, ointments, dermal gels, injectable preparations, drinkable suspensions etc.

The useful dosage can be varied according to the nature and severity of the disorder, the administration route and the age and weight of the patient and ranges from 1 to 500 mg per day in one or more administrations.

The Examples that follow illustrate the invention but do not limit it in any way.

The starting materials used are products that are known or that are prepared according to known operating procedures.

The structures of the compounds described in the Examples were determined according to the usual spectrophotometric techniques (infrared, NMR, mass spectrometry, . . . ).

EXAMPLE 1

7-[3-(1H-Tetrazol-5-yl)phenoxy]-2,3,3a,4-tetrahydro-1H-pyrrolo-[2,1-c][1,2,4]benzothiadiazine 5,5-dioxide Step A: 3-[(5,5-Dioxido-2,3-dihydro-1H-pyrrolo[2,1-c][1,2,4]benzothiadiazin-7-yl)oxy]phenol A solution of 68.75 mmol of $BBr_3$ in 25 ml of methylene chloride is added dropwise to a solution, cooled to 0° C., of 27.50 mmol of 7-methoxy-2,3-dihydro-1H-pyrrolo-[2,1-c][1,2,4]benzothiadiazine 5,5-dioxide in 350 ml of methylene chloride. Stirring is carried out at ambient temperature for 24 hours. The reaction mixture is poured into a mixture of ice and water, and the suspension is stirred for 30 minutes. The precipitate is filtered off, rinsed several times with water, filtered under suction and dried in vacuo to yield the expected product.

Melting point: >300° C. Elemental micro-analysis:

|  | C % | H % | N % | S % |
|---|---|---|---|---|
| Calculated | 50.41 | 4.23 | 11.76 | 13.46 |
| Found | 50.00 | 4.19 | 11.28 | 13.41 |

Step B: 3-[(5,5-Dioxido-2,3-dihydro-1H-pyrrolo[2,1-c][1,2,4]benzothiadiazin-7-yl)oxy]benzonitrile A suspension containing 7.06 mmol of the product described in the Step above, 11.02 mmol of 3-cyanophenylboronic acid, 11.02 mmol of copper(II) acetate, 22 mmol of pyridine and about 500 mg of 4 Å molecular sieve in 200 ml of methylene chloride is stirred for 24 hours. The reaction mixture is diluted by adding a further 100 ml of methylene chloride and the suspension is filtered. The filtrate is concentrated and then directly placed on a silica column which is eluted with a methylene chloride/methanol 95/5 system. The fractions containing the expected product are combined and evaporated, and the residue is taken up in a small amount of ethyl ether. After filtering off the solid, the expected product is recovered in the form of a white powder.

Melting point: 229-233° C. Elemental micro-analysis:

|  | C % | H % | N % | S % |
|---|---|---|---|---|
| Calculated | 60.17 | 3.86 | 12.38 | 9.45 |
| Found | 59.42 | 3.96 | 12.29 | 9.63 |

Step C: 7-[3-(1H-Tetrazol-5-yl)phenoxy]-2,3-dihydro-1H-pyrrolo[2,1-c][1,2,4]-benzothiadiazine 5,5-dioxide 0.35 mmol of di-(n-butyl)-tin oxide is added to a solution containing 3.53 mmol of the product obtained in the Step above and 7.07 mmol of azidotrimethylsilane in 50 ml of dioxane and the mixture is refluxed for 24 hours. The mixture is allowed to return to ambient temperature, the dioxane is evaporated off, the residue is redissolved in methanol and the mixture is concentrated again. The residue is taken up in ethyl acetate and extraction is carried out using 10% sodium bicarbonate solution. The basic aqueous phases are combined, washed once with ethyl acetate and acidified with 1N HCl. The white precipitate formed is filtered off to yield the expected product.

Melting point: 155° C. Elemental micro-analysis:

|  | C % | H % | N % | S % |
|---|---|---|---|---|
| Calculated | 53.40 | 3.69 | 21.98 | 8.39 |
| Found | 53.17 | 3.67 | 22.19 | 7.81 |

Step D: 7-[3-(1H-Tetrazol-5-yl)phenoxy]-2,3,3a,4-tetrahydro-1H-pyrrolo[2,1-c][1,2,4]benzothiadiazine 5,5-dioxide 10 ml of ethanol and 0.52 mmol of the product obtained in the Step above in the presence of 1.58 mmol of $NaBH_4$ are refluxed for 30 minutes. The mixture is allowed to return to ambient temperature and 10 ml of 1N HCl are added. The suspension is stirred and then filtered to yield the expected product in the form of a white powder which is recrystallised from ethanol and yields the title product.

Melting point: 266-272° C. Elemental micro-analysis:

|  | C % | H % | N % | S % |
|---|---|---|---|---|
| Calculated | 53.12 | 4.20 | 21.86 | 8.34 |
| Found | 53.14 | 4.36 | 21.93 | 8.56 |

EXAMPLE 2

7-[3-(1-Methyl-1H-tetrazol-5-yl)phenoxy]-2,3,3a,4-tetrahydro-1H-pyrrolo[2,1-c][1,2,4]benzothiadiazine 5,5-dioxide Step A: 7-[3-(1-Methyl-2H-tetrazol-5-yl)phenoxy]-2,3-dihydro-1H-pyrrolo[2,1-c][1,2,4]benzothiadiazine 5,5-dioxide 200 µl (0.39 mmol) of bis(tri-n-butyl)tin oxide are added to a suspension of the product obtained in Example 1 (300 mg, 0.78 mmol) in 20 ml of anhydrous ethanol and the solution is refluxed for 10 minutes. The ethanol is evaporated off, 1 ml of methyl iodide is added and stirring is carried out at ambient temperature overnight. The precipitate is filtered off to yield a mixture of the 1- and 2-methyl-2H-tetrazol isomers which is purified to yield the title product.

Step B: 7-[3-(1-Methyl-2H-tetrazol-5-yl)phenoxy]-2,3,3a,4-tetrahydro-1H-pyrrolo[2,1-c][1,2,4]benzothiadiazine 5,5-dioxide The procedure is as in Step D of Example 1, starting from the product obtained in Step A.
Melting point: 202-204° C. Elemental micro-analysis:

|  | C % | H % | N % | S % |
|---|---|---|---|---|
| Calculated | 54.26 | 4.55 | 21.09 | 8.05 |
| Found | 54.14 | 4.63 | 20.30 | 7.88 |

EXAMPLE 3

7-[3-(2-Methyl-2H-tetrazol-5-yl)phenoxy]-2,3,3a,4-tetrahydro1H-pyrrolo[2,1-c][1,2,4]benzothiadiazine 5,5-dioxide Step A: 7-[3-(2-Methyl-2H-tetrazol-5-yl)phenoxy]-2,3-dihydro-1H-pyrrolo[2,1-c]-[1,2,4]benzothiadiazine 5,5-dioxide 163 µl of methyl iodide diluted with 4 ml of acetonitrile are added dropwise to a solution of the product obtained in Step C of Example 1 (500 mg) in 4 ml of water and 105 mg of NaOH. The mixture is refluxed for 2 hours and the reaction mixture is allowed to return to ambient temperature. A precipitate is formed which is filtered off and which corresponds to the title product.
Elemental micro-analysis:

|  | C % | H % | N % | S % |
|---|---|---|---|---|
| Calculated | 54.54 | 4 07 | 21.20 | 8.09 |
| Found | 54.52 | 4.24 | 20.72 | 8.18 |

Step B: 7-[3-(2-Methyl-2H-tetrazol-5-yl)phenoxy]-2,3,3a,4-tetrahydro-1H-pyrrolo[2,1-c][1,2,4]benzothiadiazine 5,5-dioxide The procedure is as in Step D of Example 1, starting from the compound obtained in Step A.
Melting point: 266° C. Elemental micro-analysis:

|  | C % | H % | N % | S % |
|---|---|---|---|---|
| Calculated | 54.26 | 4.55 | 21.09 | 8.05 |
| Found | 54.06 | 4.78 | 20.01 | 8.19 |

Examples 4 to 12 which follow were prepared according to the procedure described in Example 1, using the appropriate boronic acid in Step B and converting the functional group into the heteroaryl desired.

EXAMPLE 4

7-[3-(1H-Imidazol-2-yl)phenoxy]-2,3,3a,4-tetrahydro-1H-pyrrolo-[2,1-c][1,2,4]benzothiadiazine 5,5-dioxide

EXAMPLE 5

7-[3-(1H-Imidazol-1-yl)phenoxy]-2,3,3a,4-tetrahydro-1H-pyrrolo-[2,1-c][1,2,4]benzothiadiazine 5,5-dioxide

EXAMPLE 6

7-[3-(1H-Imidazol-5-yl)phenoxy]-2,3,3a,4-tetrahydro-1H-pyrrolo-[2,1-c][1,2,4]benzothiadiazine 5,5-dioxide

EXAMPLE 7

7-[3-(1H-1,2,3-Triazol-5-yl)phenoxy]-2,3,3a,4-tetrahydro-1H-pyrrolo-[2,1-c][1,2,4]benzothiadiazine 5,5-dioxide

EXAMPLE 8

7-[3-(2H-1,2,3-Triazol-2-yl)phenoxy]-2,3,3a,4-tetrahydro-1H-pyrrolo-[2,1-c][1,2,4]benzothiadiazine 5,5-dioxide

EXAMPLE 9

7-[3-(1H-1,2,3-Triazol-1-yl)phenoxy]-2,3,3a,4-tetrahydro-1H-pyrrolo-[2,1-c][1,2,4]benzothiadiazine 5,5-dioxide

EXAMPLE 10

7-[3-(4H-1,2,4-Triazol-3-yl)phenoxy]-2,3,3a,4-tetrahydro-1H-pyrrolo-[2,1-c][1,2,4]benzothiadiazine 5,5-dioxide

EXAMPLE 11

7-[3-(1H-1,2,4-Triazol-1-yl)phenoxy]-2,3,3a,4-tetrahydro-1H-pyrrolo-[2,1-c][1,2,4]benzothiadiazine 5,5-dioxide

EXAMPLE 12

7-[3-(4H-1,2,4-Triazol-4-yl)phenoxy]-2,3,3a,4-tetrahydro-1H-pyrrolo-[2,1-c][1,2,4]benzothiadiazine 5,5-dioxide

EXAMPLE 13

3-{3-[(5,5-Dioxido-2,3,3a,4-tetrahydro-1H-pyrrolo[2,1-c][1,2,4]benzothiadiazin-7-yl)oxy]phenyl}-1,2,4-oxadiazol-5(4H)-one Step A: 3-[(5,5-Dioxido-2,3-dihydro-1H-pyrrolo[2,1-c][1,2,4]benzothiadiazin-7-yl)oxy]-N'-hydroxybenzenecarboximidamide 616 µl (4.42 mmol) of triethylamine are added to a solution of hydroxylamine hydrochloride (307 mg, 4.42 mmol) in 1.5 ml of DMSO and the suspension is stirred for 10 minutes. The precipitate is filtered off and the filtrate is concentrated. 250 mg (0.737 mmol) of the product obtained in Step B of Example 1 are then added to that filtrate and the solution is stirred at 75° C. for 16 hours. The reaction mixture is allowed to return to ambient temperature, and precipitation is brought about using water. A gummy white paste is observed which is made harder by adding $CH_2Cl_2$. The precipitate is filtered off to yield the title product.

Melting point: 165-169° C. Elemental micro-analysis:

|  | C % | H % | N % | S % |
|---|---|---|---|---|
| Calculated | 54.83 | 4.33 | 15.04 | 8.61 |
| Found | 55.07 | 4.18 | 14.66 | 8.95 |

Step B: 3-[(5,5-Dioxido-2,3-dihydro-1H-pyrrolo[2, 1-c][1,2,4]benzothiadiazin-7-yl)oxy]-N'-[(ethoxycarbonyl)oxy]benzenecarboximidamide 65 μl (0.65 mmol) of ethyl chloroformate are added dropwise to a solution, cooled to 0° C., of the product obtained in Step A (244 mg, 0.65 mmol) in 1.5 ml of DMF and 59 μl (0.72 mmol) of pyridine. Stirring is carried out at 0° C. for 30 minutes and precipitation of the reaction mixture is brought about using water. The precipitate is filtered off to yield the title product.

Melting point: 101-105° C.

Step C: 3-{3-[(5,5-Dioxido-2,3-dihydro-1H-pyrrolo [2,1-c][1,2,4]benzothiadiazin-7-yl)oxy]phenyl}-1,2, 4-oxadiazol-5(4H)-one The product obtained in the Step above (220 mg, 0.49 mmol) is stirred at the reflux of xylene (3 ml) for 2 hours. The mixture is allowed to return to ambient temperature and the precipitate is filtered off to yield the title product.

Melting point: >250° C.

Step D: 3-{3-[(5,5-Dioxido-2,3,3a,4-tetrahydro-1H-pyrrolo[2,1-c][1,2,4]benzothiadiazin-7-yl)oxy]phenyl}-1,2,4-oxadiazol-5(4H)-one The procedure is as in Step D of Example 1, starting from the product obtained in Step C.

Melting point: 241-244° C. Elemental micro-analysis:

|  | C % | H % | N % | S % |
|---|---|---|---|---|
| Calculated | 53.99 | 4.03 | 13.99 | 8.01 |
| Found | 54.28 | 4.01 | 13.50 | 7.92 |

EXAMPLE 14

3-{3-[(5,5-Dioxido-2,3,3a,4-tetrahydro-1H-pyrrolo [2,1-c][1,2,4]benzothiadiazin-7-yl)oxy]phenyl}-1,2, 4-oxadiazole-5(4H)-thione Step A: 3-{3-[(5,5-Dioxido-2,3-dihydro-1H-pyrrolo [2,1-c][1,2,4]benzothiadiazin-7-yl)oxy]phenyl}-1,2, 4-oxadiazole-5(4H)-thione To a suspension of the product obtained in Step A of Example 13 (300 mg, 0.81 mmol) in 6 ml of $CH_3CN$ there are added 239 mg (1.21 mmol) of thiocarbonyldiimidazole and then 481 μl (3.22 mmol) of DBU. The reaction solution is stirred at ambient temperature for 1 hour. Evaporation to dryness and chromatography on silica ($CH_2Cl_2$/MeOH 95/5) are carried out. After evaporating the fractions containing the product formed, the residue is triturated in MeOH and the title product is recovered by filtration.

Melting point: 228-230° C. Elemental micro-analysis:

|  | C % | H % | N % | S % |
|---|---|---|---|---|
| Calculated | 52.16 | 3.40 | 13.52 | 15.47 |
| Found | 54.27 | 3.72 | 13.43 | 15.76 |

Step B: 3-{3-[(5,5-Dioxido-2,3,3a,4-tetrahydro-1H-pyrrolo[2,1-c][1,2,4]benzothiadiazin-7-yl)oxy]phenyl}-1,2,4-oxadiazole-5(4H)-thione The procedure is as in Step D of Example 1, starting from the product obtained in Step A.

Melting point: 231-235° C. Elemental micro-analysis:

|  | C % | H % | N % | S % |
|---|---|---|---|---|
| Calculated | 51.91 | 3.87 | 13.45 | 15.40 |
| Found | 51.68 | 3.98 | 13.07 | 15.49 |

EXAMPLE 15

7-[3-(2-Oxido-3H-1,2,3,5-oxathiadiazol4-yl)phenoxy]-2,3,3a,4-tetrahydro-1H-pyrrolo[2,1-c][1,2,4] benzothiadiazine 5,5-dioxide Step A: 7-[3-(2-Oxido-3H-1,2,3,5-oxathiadiazol-4-yl)phenoxy]-2,3-dihydro-1H-pyrrolo[2,1-c][1,2,4] benzothiadiazine 5,5-dioxide To a suspension, cooled to 0° C., of the product obtained in Step A of Example 13 (250 mg, 0.67 mmol) in 15 ml of THF there are added 109 μl (1.34 mmol) of pyridine and then, dropwise, 72 μl (1.01 mmol) of thionyl chloride dissolved in 3 ml of $CH_2Cl_2$. Stirring is carried out at 0° C. for 30 minutes and the mixture is allowed to come back to ambient temperature whilst stirring for a further hour. Evaporation to dryness is carried out and the residue is made more solid by triturating it in water. The precipitate is filtered off to yield the title product.

Step B: 7-[3-(2-Oxido-3H-1,2,3,5-oxathiadiazol-4-yl)phenoxy]-2,3,3a,4-tetrahydro-1H-pyrrolo[2,1-c] [1,2,4]benzothiadiazine 5,5-dioxide The procedure is as in Step D of Example 1, starting from the product obtained in Step A.

Melting point: 178-182° C. Elemental micro-analysis:

|  | C % | H % | N % | S % |
|---|---|---|---|---|
| Calculated | 48.56 | 3.84 | 13.32 | 15.25 |
| Found | 48.62 | 3.84 | 13.27 | 15.49 |

EXAMPLE 16

7-[3-(2-Furyl)phenoxy]-2,3,3a,4-tetrahydro-1H-pyrrolo[2,1-c][1,2,4]benzothiadiazine 5,5-dioxide

Step A: 7-(3-Bromophenoxy)-2,3-dihydro-1H-pyrrolo[2,1-c][1,2,4]benzothiadiazine 5,5-dioxide The procedure is as in Step B of Example 1, using as starting materials (3-bromophenyl)boronic acid and the product obtained in Step A of Example 1.

Step B: 7-[3-(2-Furyl)phenoxy]-2,3-dihydro-1H-pyrrolo[2,1-c][1,2,4]benzothiadiazine 5,5-dioxide A suspension of the product obtained in Step A (200 mg, 0.50 mmol), 222 µl (0.66 mmol) of 2-(tributylstannyl)furan and 30 mg (0.025 mmol) of tetrakistriphenylphosphine in 4 ml of toluene is refluxed for 45 minutes. The toluene is evaporated off in vacuo and the residue is chromatographed on $SiO_2$ ($CH_2Cl_2$/acetone 96/4) to yield the title product.
Melting point: 186-189° C. Elemental micro-analysis.

|  | C % | H % | N % | S % |
| --- | --- | --- | --- | --- |
| Calculated | 63.15 | 4.24 | 7.36 | 8.43 |
| Found | 62.85 | 4.22 | 7.37 | 8.40 |

Step C: 7-[3-(2-Furyl)phenoxy]-2,3,3a,4-tetrahydro-1H-pyrrolo[2,1-c][1,2,4]benzothiadiazine 5,5-dioxide The procedure is as in Step D of Example 1, starting from the product obtained in Step B.
Melting point: 178-180° C. Elemental micro-analysis:

|  | C % | H % | N % | S % |
| --- | --- | --- | --- | --- |
| Calculated | 62.81 | 4.74 | 7.32 | 8.38 |
| Found | 63.11 | 4.82 | 7.28 | 8.34 |

EXAMPLE 17

7-[3-(3-Furyl)phenoxy]-2,3,3a,4-tetrahydro-1H-pyrrolo[2,1-c][1,2,4]benzothiadiazine 5,5-dioxide

Step A: 7-[3-(3-Furyl)phenoxy]-2,3-dihydro-1H-pyrrolo[2,1-c][1,2,4]benzothiadiazine 5,5-dioxide A suspension of the product obtained in Step A of Example 16 (300 mg, 0.76 mmol), 111 mg (0.99 mmol) of 3-furanboronic acid, 137 mg (0.99 mmol) of $K_2CO_3$ and 45 mg (0.038 mmol) of tetrakistriphenylphosphine in a mixture of 6 ml of ethanol and 1.8 ml of water is heated at 80° C. for 3 hours under $N_2$. The ethanol is evaporated off in vacuo and the residue is taken up in water and 1N HCl. The precipitate is filtered off to yield the title product.
Melting point: 128-132° C.

Step B: 7-[3-(3-Furyl)phenoxy]-2,3,3a,4-tetrahydro-1H-pyrrolo[2,1-c][1,2,4]benzothiadiazine 5,5-dioxide The procedure is as in Step D of Example 1, starting from the product obtained in Step A.
Melting point: 186-189° C. Elemental micro-analysis:

|  | C % | H % | N % | S % |
| --- | --- | --- | --- | --- |
| Calculated | 62.81 | 4.74 | 7.32 | 8.38 |
| Found | 62.43 | 4.77 | 7.33 | 8.43 |

EXAMPLE 18

7-[3-(1,3-Oxazol-5-yl)phenoxy]-2,3,3a,4-tetrahydro-1H-pyrrolo-[2,1-c][1,2,4]benzothiadiazine 5,5-dioxide The procedure is as in Example 17, replacing the 3-furanboronic acid in Step A by 1,3-oxazol-5-ylboronic acid.
Melting point: 210° C. Elemental micro-analysis:

|  | C % | H % | N % | S % |
| --- | --- | --- | --- | --- |
| Calculated | 59.52 | 4.47 | 10.96 | 8.36 |
| Found | 59.47 | 4.51 | 10.68 | 8.74 |

EXAMPLE 19

7-(3-Pyridin-2-ylphenoxy)-2,3,3a,4-tetrahydro-1H-pyrrolo[2,1-c][1,2,4]benzothiadiazine 5,5-dioxide

Step A: 7-(3-Pyridin-2-ylphenoxy)-2,3-dihydro-1H-pyrrolo[2,1-c][1,2,4]benzothiadiazine 5,5-dioxide The procedure is as in Step B of Example 16, using 2-(tributylstannyl)pyridine as starting material.
Melting point: 205-207° C.

Step B: 7-(3-Pyridin-2-ylphenoxy)-2,3,3a,4-tetrahydro-1H-pyrrolo[2,1-c][1,2,4]-benzothiadiazine 5,5-dioxide The procedure is as in Step D of Example 1, starting from the product obtained in Step A.
Melting point: 129° C. Elemental micro-analysis:

|  | C % | H % | N % | S % |
| --- | --- | --- | --- | --- |
| Calculated | 64.10 | 4.87 | 10.68 | 8.15 |
| Found | 64.30 | 5.07 | 10.55 | 7.71 |

EXAMPLE 20

7-[3-(1H-Pyrrol-1-yl)phenoxy]-2,3,3a,4-tetrahydro-1H-pyrrolo-[2,1-c][1,2,4]-benzothiadiazine 5,5-dioxide 250 mg (0.75 mmol) of {3-[(5,5-dioxido-2,3,3a,4-tetrahydro-1H-pyrrolo[2,1-c][1,2,4]-benzothiadiazin-7-yl)oxy]phenyl}amine and 137 µl (1.06 mmol) of 2,5-dimethoxytetra-hydrofuran are added to a two-phase mixture of 2.5 ml of water, 1.25 ml of AcOH and 3.75 ml of dichloro-1, 2-ethane. Stirring is carried out at 80° C. for 1 hour; the mixture is allowed to return to ambient temperature and is extracted with $CH_2Cl_2$. The organic phase is washed with saturated aqueous NaCl solution and dried over $MgSO_4$. The title product is purified by chromatography on a silica column ($CH_2Cl_2$/heptane 70/30).

Melting point: 169-170° C. Elemental micro-analysis:

|  | C % | H % | N % | S % |
|---|---|---|---|---|
| Calculated | 62.97 | 5.02 | 11.02 | 8.41 |
| Found | 63.14 | 5.18 | 10.85 | 8.15 |

EXAMPLE 21

7-(3-Morpholin4-ylphenoxy)-2,3,3a,4-tetrahydro-1H-pyrrolo[2,1-c][1,2,4]benzothiadiazine 5,5-dioxide A mixture of 300 mg (0.90 mmol) of {3-[(5,5-dioxido-2, 3,3a,4-tetrahydro-1H-pyrrolo-[2,1-c][1,2,4]benzothiadiazin-7-yl)oxy]phenyl}amine, 192 mg of $Na_2CO_3$ (1.81 mmol), 5 mg of NaI, 126 μl of 2-bromoethyl ether (0.905 mmol) in 6 ml of $CH_3CN$ is refluxed overnight. The suspension is filtered; the filtrate is evaporated, taken up in $CH_2Cl_2$ and washed with saturated NaCl solution. After evaporation in vacuo, the expected product is purified by chromatography on silica ($CH2Cl_2$/acetone 96/4).

Melting point: 199-202° C. Elemental micro-analysis:

|  | C % | H % | N % | S % |
|---|---|---|---|---|
| Calculated | 59.83 | 5.77 | 10.47 | 7.99 |
| Found | 59.38 | 6.05 | 10.31 | 8.03 |

EXAMPLE 22

7-[4-(1H-Tetrazol-5-yl)phenoxy]-2,3,3a,4-tetrahydro-1H-pyrrolo-[2,1-c][2,4]benzothiadiazine 5,5-dioxide Step A: 4-[(5,5-Dioxido-2,3-dihydro-1H-pyrrolo[2, 1-c][1,2,4]benzothiadiazin-7-yl)-oxy]benzonitrile The procedure is as in Step B of Example 1, replacing the 3-cyanophenylboronic acid by 4-cyanophenylboronic acid.
Melting point: 239-242° C.

Step B: 7-[4-(1H-Tetrazol-5-yl)phenoxy]-2,3-dihydro-1H-pyrrolo[2,1-c][1,2,4]-benzothiadiazine 5,5-dioxide The procedure is as Step C of Example 1, using the product obtained in Step A as starting material.

Step C: 7-[4-(1H-Tetrazol-5-yl)phenoxy]-2,3,3a,4-tetrahydro-1H-pyrrolo[2,1-c][1,2,4]benzothiadiazine 5,5-dioxide The procedure is as in Step D of Example 1, using the product obtained in Step B as starting material.

Melting point: 215-219° C. Elemental micro-analysis:

|  | C % | H % | N % | S % |
|---|---|---|---|---|
| Calculated | 53.12 | 4.20 | 21.86 | 8.34 |
| Found | 33.98 | 4.11 | 21.32 | 8.68 |

EXAMPLE 23

5-{3-[(5,5-Dioxido-2,3,3a,4-tetrahydro-1H-pyrrolo[2,1-c][1,2,4]benzothiadiazin-7-yl)oxy]phenyl}-1,3,4-oxadiazol-2(3H)-one Step A: Methyl 3-[(5,5-Dioxido-2,3-dihydro-1H-pyrrolo[2,1-c][1,2,4]benzothiadiazin-7-yl)oxy]benzoate The procedure is as in Step B of Example 1, replacing the 3-cyanophenylboronic acid by [3-(methoxycarbonyl)phenyl]boronic acid.

Melting point: 239-242° C. Elemental micro-analysis:

|  | C % | H % | N % | S % |
|---|---|---|---|---|
| Calculated | 58.06 | 4.33 | 7.52 | 8.61 |
| Found | 52.53 | 4.01 | 7.84 | 9.00 |

Step B: 3-[(5,5-Dioxido-2,3-dihydro-1H-pyrrolo[2, 1-c][1,2,4]benzothiadiazin-7-yl)oxy]benzohydrazide A suspension of 500 mg (1.34 mmol) of the product obtained in Step A and 978 μl (20.13 mmol) of hydrazine monohydrate in a mixture of MeOH (30 ml) and DMF (6 ml) is refluxed for 24 hours. The MeOH is evaporated off, water is added to the reaction mixture and the precipitate, which corresponds to the title product, is filtered off.

Melting point: 197-201° C.

Step C: 5-{3-[(5,5-Dioxido-2,3-dihydro-1H-pyrrolo[2,1-c][1,2,4]benzothiadiazin-7-yl)oxy]phenyl}-1,3,4-oxadiazol-2(3H)-one A suspension of 150 mg (0.40 mmol) of the product obtained in Step B, 85 mg (0.52 mmol) of 1,1'-carbonyldiimidazole and 95 μl (0.68 mmol) of $Et_3N$ in a mixture of THF (3.7 ml) and DMF (3.7 ml) is refluxed for 3 hours. The mixture is allowed to return to ambient temperature and is acidified with 1N HCl. A white precipitate forms, which is filtered off to yield the title product.

Step D: 5-{3-[(5,5-Dioxido-2,3,3a,4-tetrahydro-1H-pyrrolo[2,1-c][1,2,4]benzothiadiazin-7-yl)oxy]phenyl}-1,3,4-oxadiazol-2(3H)-one The procedure is as in Step D of Example 1, starting from the product obtained in Step C.

Melting point: 254-258° C. Elemental micro-analysis:

|  | C % | H % | N % | S % |
|---|---|---|---|---|
| Calculated | 53.99 | 4.03 | 13.99 | 8.01 |
| Found | 54.31 | 4.27 | 13.24 | 7.72 |

Pharmacological Study of Products of the Invention

Study of the excitatory currents induced by AMPA in Xenopus oocytes a—Method:

mRNA's are prepared from cerebral cortex of male Wistar rats by the guanidinium thiocyanate/phenol/chloroform method. The poly (A$^+$) mRNA's are isolated by chromatography on oligo-dT cellulose and injected at a level of 50 ng per oocyte. The oocytes are incubated for 2 to 3 days at 18° C. to permit expression of the receptors and are then stored at 8-10° C.

Electrophysiological recording is carried out in a Plexiglass® chamber at 20-24° C. in OR2 medium (J. Exp. Zool., 1973, 184, 321-334) by the "voltage-clamp" method using two electrodes, with a third electrode placed in the bath serving as reference.

All the compounds are applied via the incubation medium and the electric current is measured at the end of the application period. AMPA is used in a concentration of 10 μM. For each compound studied, the concentration that doubles (EC2X) or quintuples (EC5X) the intensity of the current induced by AMPA alone (5 to 50 nA) is determined.

b—Results:

The compounds of the invention potentiate the excitatory effects of AMPA to a very considerable degree and their activity is very clearly superior to that of compounds of reference. The compound of Example 1 especially has an EC2X of 0.2 μM and an EC5X of 0.8 μM, the compound of Example 17 an EC2X of 4.5 μM and an EC5X of 11.5 μM, the compound of Example 18 an EC2X of 0.66 μM and an EC5X of 4 μM.

| PHARMACEUTICAL COMPOSITION | |
|---|---|
| Formula for the preparation of 1000 tablets each containing 100 mg of 7-[3-(3-furyl)-phenoxy]-2,3,3a,4-tetrahydro-1H-pyrrolo[2,1-c][1,2,4]benzothiadiazine 5,5-dioxide (Example 17) | 100 g |
| hydroxypropylcellulose | 2 g |
| wheat starch | 10 g |
| lactose | 100 g |
| magnesium stearate | 3 g |
| talc | 3 g |

We claim:

1. A compound selected from those of formula (I):

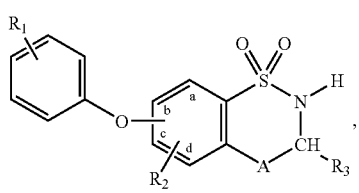

wherein:
R$_1$ represents a heterocyclic group,
R$_2$ represents hydrogen, halogen, or hydroxy, A represents NR$_4$, and R$_3$ and R$_4$, together with the carbon and nitrogen atoms to which they are attached, form a ring

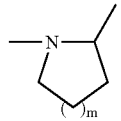

wherein m represents 1, 2, or 3,
its enantiomers and diastereoisomers, and addition salts thereof with a pharmaceutically-acceptable acid or base,
it being understood that a heterocyclic group may be a monocyclic or bicyclic, aromatic or non-aromatic group containing from one to four identical or different hetero atoms selected from nitrogen, oxygen, and sulphur, optionally substituted by one or more identical or different groups selected from halogen, linear or branched (C$_1$-C$_6$)alkyl, linear or branched (C$_1$-C$_6$)alkoxy, linear or branched (C$_1$-C$_6$)polyhaloalkyl, linear or branched (C$_1$-C$_6$)alkoxy-carbonyl, oxo, thioxo, carboxy, linear or branched (C$_1$-C$_6$)acyl, linear or branched (C$_1$-C$_6$)polyhaloalkoxy, hydroxy, cyano, nitro, amino optionally substituted by one or more linear or branched (C$_1$-C$_6$)alkyl groups, aminosulphonyl optionally substituted by one or more linear or branched (C$_1$-C$_6$)alkyl groups, and (C$_1$-C$_6$)alkylsulphonylamino.

2. A compound of claim 1, wherein R$_2$ represents hydrogen.

3. A compound of claim 1, wherein the grouping

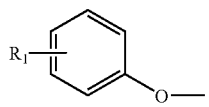

is in position b of the phenyl ring carrying it.

4. A compound of claim 1, wherein R$_1$ is a monocyclic heterocyclic group.

5. A compound of claim 1, wherein R$_1$ is an aromatic monocyclic heterocyclic group.

6. A compound of claim 1, wherein R$_1$ is tetrazolyl, furyl or oxazolyl.

7. A compound of claim 1, wherein R$_1$ is in the meta-position of the phenoxy ring structure carrying it.

8. A compound of claim 1, wherein R$_1$, is in the para-position of the phenoxy ring structure carrying it.

9. A compound of claim 1, wherein m represents 1.

10. A compound of claim 1 which is selected from 7-[3-(1H-tetrazol-5-yl) phenoxy]-2,3,3a,4-tetrahydro-1H-pyrrolo[2, 1-c][1,2,4]benzothiadiazine 5,5-dioxide, its enantiomers, and addition salts thereof with a pharmaceutically-acceptable acid or base.

11. A compound of claim 1 which is selected from 7-[3-(3-(3-furyl)phenoxy]-2,3,3a,4-tetrahydro-1H-pyrrolo[2,1-c][1,2,4]benzothiadiazine 5,5-dioxide, its enantiomers, and addition salts thereof with a pharmaceutically-acceptable acid or base.

12. A compound of claim 1 which is selected from 7-[3-(1,3-oxazol-5-yl) phenoxy]-2,3,3a,4-tetrahydro-1H-pyrrolo[2,1-c][1,2,4]benzothiadiazine.

13. A method for treating a living animal body, including a human, afflicted with a condition selected from anxiety and depression, comprising the step of administering to the living animal body, including a human, an amount of a compound of claim 1 which is effective for alleviation of the condition.

14. A pharmaceutical composition comprising as active principle an effective amount of a compound of claim 1, together with one or more pharmaceutically-acceptable excipients or vehicles.

* * * * *